US008478416B2

(12) United States Patent
Zierhofer

(10) Patent No.: US 8,478,416 B2
(45) Date of Patent: Jul. 2, 2013

(54) IMPLANT POWER CONTROL

(75) Inventor: Clemens M. Zierhofer, Kundl (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 47 days.

(21) Appl. No.: 12/942,698

(22) Filed: Nov. 9, 2010

(65) Prior Publication Data

US 2011/0112607 A1 May 12, 2011

Related U.S. Application Data

(60) Provisional application No. 61/259,850, filed on Nov. 10, 2009.

(51) Int. Cl.
*A61N 1/00* (2006.01)
(52) U.S. Cl.
USPC ............................................................ 607/57
(58) Field of Classification Search
None
See application file for complete search history.

(56) References Cited

U.S. PATENT DOCUMENTS

| | | | | |
|---|---|---|---|---|
| 4,726,378 | A | 2/1988 | Kaplan | 128/419 R |
| 5,217,011 | A | 6/1993 | Bisch | 128/420.6 |
| 6,178,353 | B1 | 1/2001 | Griffith et al. | 607/61 |
| 6,308,101 | B1 * | 10/2001 | Faltys et al. | 607/57 |
| 7,212,863 | B2 | 5/2007 | Strandberg | 607/30 |
| 2002/0019669 | A1 | 2/2002 | Berrang et al. | 623/10 |
| 2003/0050676 | A1 | 3/2003 | Hubelbank et al. | 607/60 |
| 2003/0171790 | A1 | 9/2003 | Nelson et al. | 607/60 |
| 2005/0033383 | A1 * | 2/2005 | Ibrahim et al. | 607/57 |
| 2005/0143783 | A1 | 6/2005 | Boveja et al. | 607/40 |
| 2006/0210104 | A1 | 9/2006 | Shennib et al. | 381/315 |
| 2006/0244560 | A1 | 11/2006 | Zimmerling et al. | 335/207 |
| 2008/0002834 | A1 | 1/2008 | Hochmair | 381/71.2 |
| 2009/0157146 | A1 | 6/2009 | Linder et al. | 607/60 |

FOREIGN PATENT DOCUMENTS

EP 1704894 9/2006

OTHER PUBLICATIONS

International Searching Authority, International Search Report—International Application No. PCT/US2010/056002, dated Jan. 10, 2011, together with the Written Opinion of the International Searching Authority, 9 pages.
European Patent Office, Supplemental European Search Report—Application No. 10830592.1-1652 dated Apr. 2, 2013, 8 pages.

\* cited by examiner

*Primary Examiner* — Christopher D Koharski
*Assistant Examiner* — Nadia Ahmad
(74) *Attorney, Agent, or Firm* — Sunstein Kann Murphy & Timbers LLP

(57) ABSTRACT

A system and method of operating an implant system having an external portion and an implanted portion. The external portion includes a first magnet and a power signal transmission module for transmitting an electrical power signal across the skin of a user. The implanted portion including a second magnet, a receiver module for receiving the power signal across the skin of a user, a Hall Sensor, a switch, and a battery. The method includes externally orientating and/or positioning the first magnet in a first arrangement, such that the external portion is held in place on the user based substantially on a magnetic force between the first magnet and the second magnet, and such that the power signal transmission module is aligned with the receiver module and the receiver module receives the power signal. The first magnet is orientated and/or positioned in a second arrangement, such that the first magnet applies a magnetic field that is sensed by the Hall Sensor. The switch in the implanted portion is controlled based, at least in part, on output from the Hall Sensor, the switch for providing power from the battery.

14 Claims, 3 Drawing Sheets

IMPLANT POWER CONTROL

CROSS REFERENCE TO RELATED APPLICATIONS

The present application claims priority from U.S. provisional application Ser. No. 61/259,850, entitled "Implant Power Control," filed Nov. 10, 2009, which is hereby incorporated herein by reference in its entirety.

TECHNICAL FIELD

The present invention relates to implants, and more particularly, to a system and methodology to switch power on/off in an implant.

BACKGROUND ART

Cochlear implants and other inner ear prostheses are one option to help profoundly deaf or severely hearing impaired persons. Unlike conventional hearing aids that just apply an amplified and modified sound signal; a cochlear implant is based on direct electrical stimulation of the acoustic nerve. Typically, a cochlear implant stimulates neural structures in the inner ear electrically in such a way that hearing impressions most similar to normal hearing is obtained.

More particularly, a normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Some persons have partial or full loss of normal sensorineural hearing. Cochlear implant systems have been developed to overcome this by directly stimulating the user's cochlea 104. A typical cochlear prosthesis may include two parts: the speech processor 111 and the implanted stimulator 108. The speech processor 111 typically includes a microphone, a power supply (batteries) for the overall system and a processor that is used to perform signal processing of the acoustic signal to extract the stimulation parameters. The speech processor may be a behind-the-ear (BTE-) device.

The stimulator 108 generates the stimulation patterns (based on the extracted audio information) that are sent through an electrode lead 109 to an implanted electrode array 110. Typically, this electrode array 110 includes multiple electrodes on its surface that provide selective stimulation of the cochlea 104. For example, each electrode of the cochlear implant is often stimulated with signals within an assigned frequency band based on the organization of the inner ear. The placement of each electrode within the cochlea is typically based on its assigned frequency band, with electrodes closer to the base of the cochlea generally corresponding to higher frequency bands.

The connection between speech processor and stimulator is usually established by means of a radio frequency (RF-) link. Note that via the RF-link both stimulation energy and stimulation information are conveyed. Typically, digital data transfer protocols employing bit rates of some hundreds of kBit/s are used.

A totally implantable cochlear implant (TICI) is a cochlear implant system without permanently used external components such as an external speech processor. The implantable TICI typically includes a microphone and subsequent stages perform audio signal processing for the implementation of a particular stimulation strategy (e.g., CIS). It also includes stimulation electrodes, power management electronics, and a coil for the transcutaneous transmission of RF signals.

Unlike a pacemaker implant, the power supply of a TICI generally cannot be established by means of a non-rechargeable battery. This is because the overall pulse repetition rate of a TICI is much higher. For example, typically about 20 kpulses/s are generated by a cochlear implant using CIS, as compared to about 1 pulse/s in a pacemaker. Besides, a cochlear implant typically performs complex audio signal processing, as compared to simple sensing tasks performed in a pacemaker. Consequently, a rechargeable battery is typically required in a TICI, which needs recharging after a particular time period of operation. To recharge the battery, an external device is often used for transcutaneous transmission of RF/power signals.

As shown in FIG. 2, an external part 201 includes a first magnet 205. A TICI 202 located under the skin 203 and embedded in bone 204 typically includes a second magnet 206 and a coil 208. The first magnet 205 is positioned over the second magnet 206 such that the external part 201 is held against the implant 202 in an optimum position. By maintaining such a position, an external coil 207 associated with external part 201 can, via inductive coupling, transmit power to the coil 208 of implant 202.

At various times, such as when sleeping or during an emergency, it may be desirable for the user to turn the TICI off for purposes of, without limitation, safety or power conservation. In addition to turning the TICI off, the capability to turn the TICI back on is often equally desirable. However, external control of the TICI is currently inhibited since the external component provides power, but not data/control information.

SUMMARY OF THE INVENTION

In accordance with an embodiment of the invention, an implant system includes an implantable portion having a battery. A switch provides power from the battery. The switch is controlled, at least in part, by output from a Hall sensor.

In accordance with related embodiments of the invention, the implant system may further include an external portion having a first magnet. The magnet applies a magnetic field to the Hall sensor so as to control the switch. For example, when the first magnet is oriented at a first polarity relative to the Hall sensor, the switch may be controlled such that power from the battery is interrupted. Furthermore, when the first magnet is oriented at a second polarity relative to the Hall sensor, the switch may be controlled such that power from the battery is turned on.

The external portion may further includes a power signal transmission module for transmitting the electrical power signal across the skin of a user, with the implantable portion further including both a second magnet and a receiver module for receiving the power signal across the skin of a user. When the first magnet is aligned and/or orientated in a first arrangement, the external portion is held in place on the user based substantially on the magnetic forces between the first magnet and the second magnet, so as to align the power signal transmission module and the receiver module. The first magnet may apply a magnetic field to the Hall sensor when in a second arrangement (of orientation and/or position) relative to the user, so as to control the switch. The battery may be rechargeable, and the power signal received by the receiver may be used to recharge the battery.

In accordance with further related embodiments of the invention, the implant system may be a cochlear implant, with the implantable portion including a stimulator module for producing for the auditory system of the user an electrical stimulation signal representative of an acoustic signal. The stimulator module may be powered by the battery via the switch. The stimulator module may include an electrode array, a microphone for receiving acoustic signals, and a signal processor. The signal processor converts acoustic signals received by the microphone into the electrical stimulation signal representative of the acoustic signal, the signal processor stimulating the electrode array with the electrical stimulation signal.

In accordance with another embodiment of the invention, a method of operating an implant system includes externally positioning a first magnet proximate an implanted portion of the implant system, such that the magnet is sensed by a Hall Sensor within the implanted portion. A switch in the implanted portion is controlled based, at least in part, on output from the Hall Sensor, the switch for providing power from a battery.

In accordance with related embodiments of the invention, externally positioning the first magnet may include orienting the first magnet to be at a first polarity relative to the Hall sensor, whereby the switch is controlled such that power from the battery is interrupted. Externally positioning the first magnet to be at a second polarity relative to the Hall sensor may control the switch such that power from the battery is turned on.

In accordance with further related embodiments of the invention, an external portion of the implant system may include both the first magnet and a power signal transmission module for transmitting the electrical power signal across the skin of a user, with the implanted portion further including both a second magnet and a receiver module for receiving the power signal across the skin of a user. The method may further include positioning the first magnet in a first arrangement (of orientation and/or position) such that the external portion is held in place on the user based substantially on the magnetic forces between the first magnet and the second magnet, so as to align the power signal transmission module and the receiver module. The battery may be recharged with the power signal received by the receiver. The first magnet may be positioned in a second arrangement (of orientation and/or position) relative to the user, such that the first magnet applies a magnetic field to the Hall sensor.

In accordance with yet further related embodiments of the invention, the implantable portion may be a cochlear implant, with the method further including producing for the auditory system of a user of the cochlear implant an electrical stimulation signal representative of an acoustic signal. Producing the electrical stimulation signal may include converting acoustic signals received by an implanted microphone, and stimulating an electrode array with the electrical stimulation signal.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments of the invention, an implant includes a Hall sensor for controlling switching of power. Details are discussed below.

Figure 3:
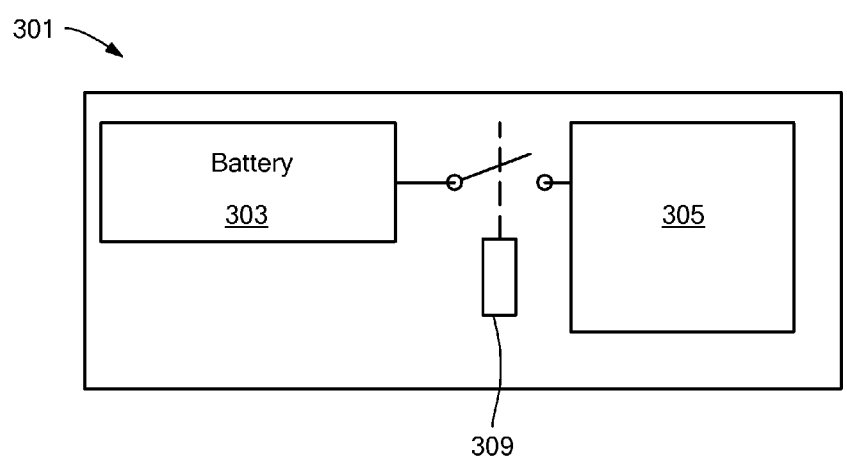
FIG. 3 is a graphical illustration of an implant that includes a Hall sensor, in accordance with an embodiment of the invention.

FIG. 3 is a graphical illustration of an implant 301 that includes a Hall sensor 309 whose output is used for controlling, at least in part, switching of power, in accordance with an embodiment of the invention. The implant may be one of a variety of implants, including, without limitation, a cochlear implant, a defibrillator, a cardioverter, a pacemaker, and a retinal implant.

The Hall sensor 309 varies its output voltage in response to various changes in the sensed magnetic field including, without limitation, polarity. The Hall sensor 309 is used, for example, in combination with circuitry and/or software, to control a switch 311 that couples power from battery 303 to electronic circuitry 305 upon sensing a magnetic field. The combination of the Hall sensor 309 and switch 311 is often referred to as a Hall Switch.

Illustratively, Hall sensor 309 and switch 311 may be implemented in a totally implantable cochlear implant (TICI) of a user, such that an external magnet may advantageously be used to switch power supplied to at least some of the implant's electronic circuitry. For example, a TICI user may interrupt power to circuitry within the TICI when sleeping, so as to conserve power in the TICI's rechargeable battery, or shut down the TICI during an emergency for safety purposes.

In various embodiments of the invention, when the external magnet is oriented at a first polarity relative to the Hall sensor 309 of the TICI, output from the Hall sensor 309 may be used, in part, to control the switch 311 such that, for example, power between the battery 303 and the electronic circuitry 305 is interrupted. When the external magnet is oriented at a second polarity relative to the Hall sensor 309, the switch 311 may be controlled, for example, such that, power from the battery 303 is provided to the electronic circuitry 305. In various embodiments, the switch 311 may alternate between positions based on sensing changes in the presence and/or lack of a magnetic field of the same polarity. The switch may latch in position, such that the position of the switch does not change upon removal of the magnetic field created by the external magnet.

Figure 1:
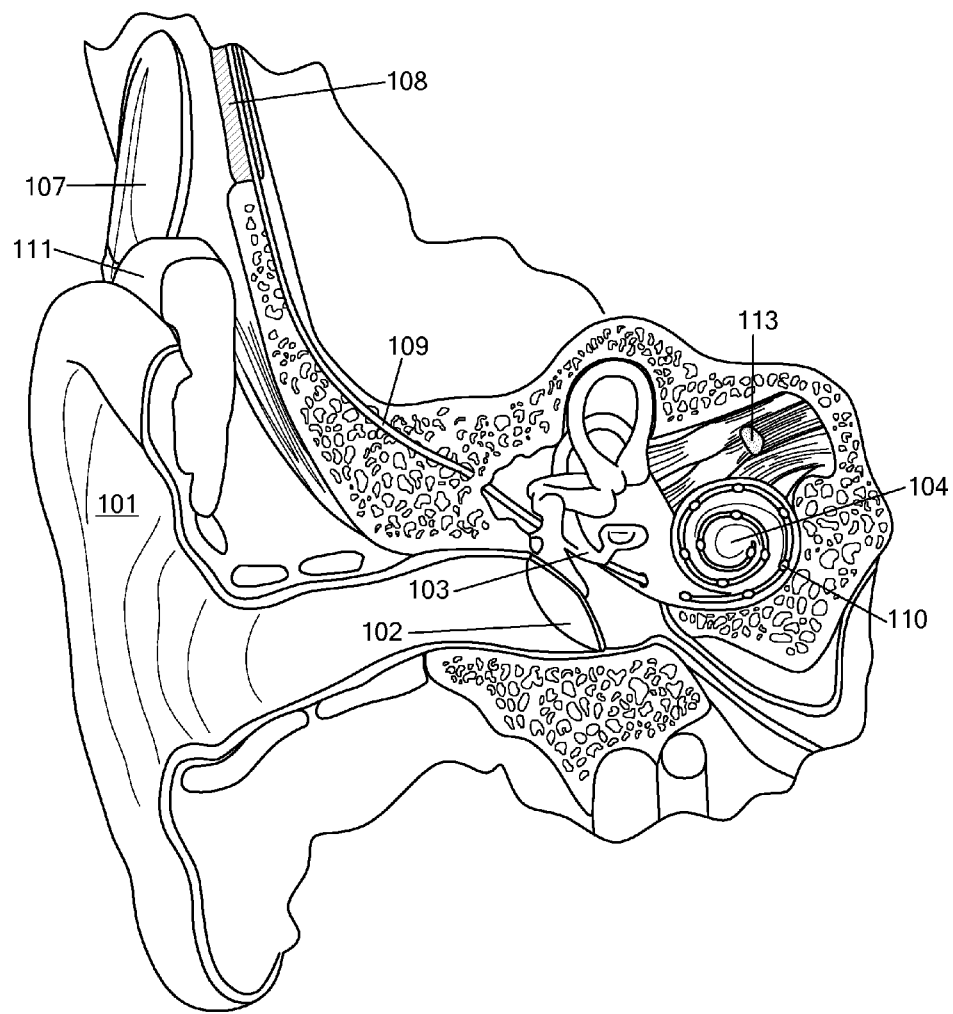
FIG. 1 illustrates a sectional view of an ear connected to a cochlear implant system (PRIOR ART)
Figure 2:
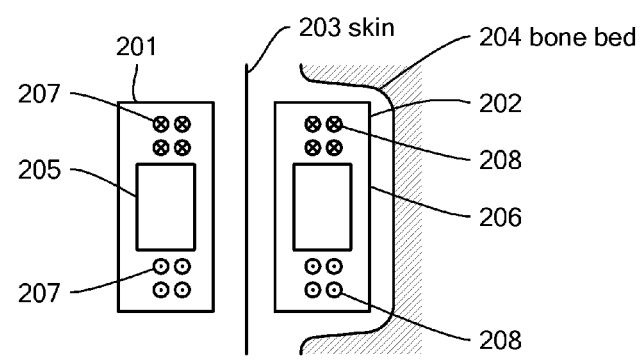
FIG. 2 is a graphical illustration of a Totally Implantable Cochlear Implant (TICI) and external part used for transfer of power (PRIOR ART)

Referring back to FIG. 2, the TICI may utilize an external device 205 for transmitting an electrical power signal across the skin of a user, which is then utilized by the TICI to supply power and/or recharge the rechargeable battery 303. The external device 205 may include, for example, a first magnet 205, and a power transmission module having a coil 207 for transmitting the electrical power signal across the skin of the user. The implantable portion of the TICI may include a second magnet 206, and a receiver module with a coil 202 for receiving the power signal across the skin of a user. When the first magnet is placed in a first arrangement (of orientation and/or position), the external device 205 is held in place on the user based substantially on the magnetic forces between the first magnet 206 and the second magnet 205, so as to align the coils of the power signal transmission module and the receiver module.

Figure 4:
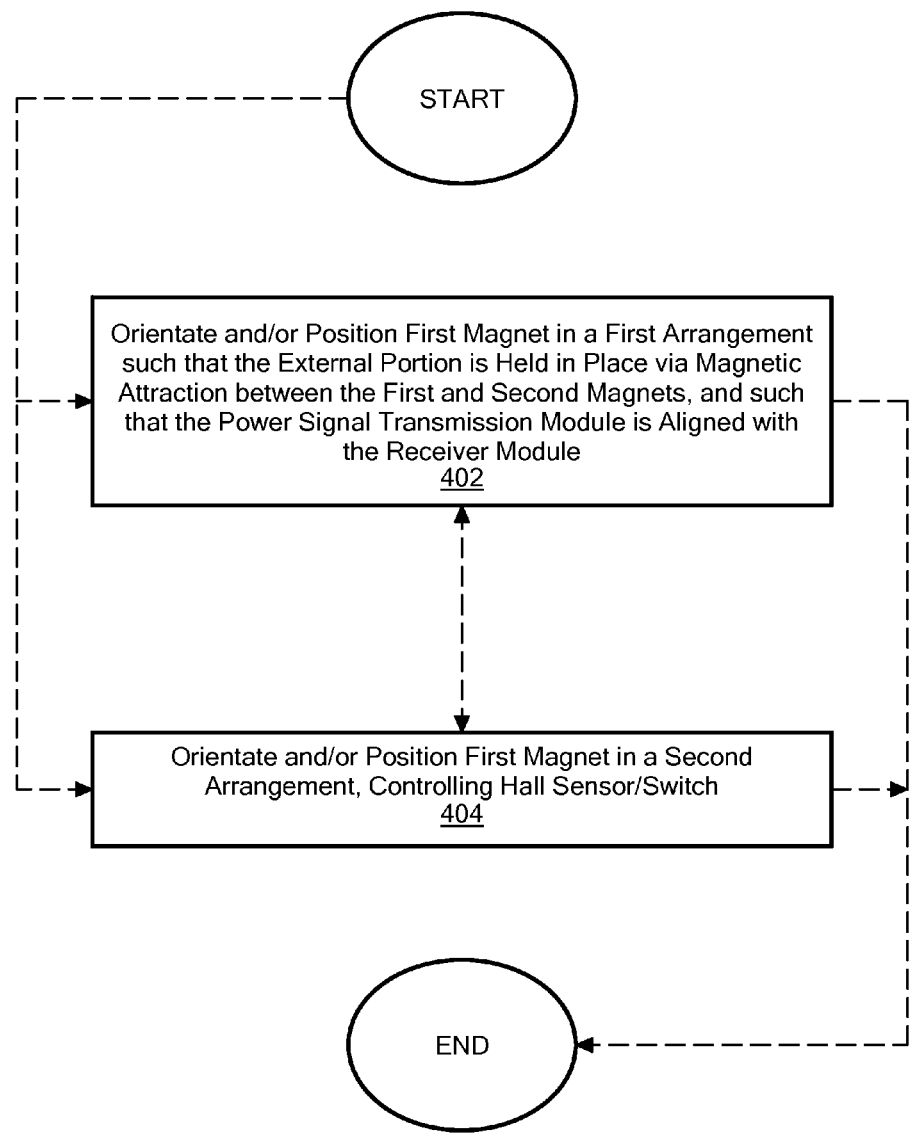
FIG. 4 shows a process in which the first magnet is used to both hold the external portion of the implant in place on the user, and to activate the Hall sensor and control the switching of power within the TICI, in accordance with an embodiment of the invention.

In illustrative embodiments, the first magnet 205, in addition to being used to hold the external portion of the implant in place on the user, may be further used to activate the Hall sensor and control the switching of power within the TICI, as shown in FIG. 4. For example, when the first magnet 206 is orientated and/or positioned in a first arrangement (of orientation and/or position), step 402, the external device 205 is held in place on the user based substantially on the magnetic forces between the first magnet 206 and the second magnet 205, so as to align the coils of the power signal transmission module and the receiver module, as described above. Upon orientating and/or positioning the first magnet 206 in a second arrangement (of orientation and/or position), step 404, the output from the Hall sensor 309 may control switch 311 such that, for example, power is provided or interrupted to various electronic circuitry within the TICI. In various embodiments, the first magnet may be flipped (compared to when the first magnet is used to hold/align the external device) so as to provide a different polarity and thus control the switch. The Hall sensor 309 is used, for example, in combination with circuitry and/or software, to control a switch 311 that couples power from battery 303 to electronic circuitry 305 upon sensing a magnetic field.

The implantable portion of a cochlear implant typically includes a stimulator modulator, which may have a signal processor that produces for the auditory system of the user an electrical stimulation signal representative of an acoustic signal. An electrode array is operationally coupled to the signal processor, which stimulates the electrode array with the electrical stimulation signal. Additionally, a TICI may include a microphone for receiving acoustic signals, which are forwarded to the signal processor. The Hall sensor 309 and switch 311 may be used to turn on, or interrupt power, to any of the above-described electronic circuitry 305 upon sensing the magnetic field.

The embodiments of the invention described above are intended to be merely exemplary; numerous variations and modifications will be apparent to those skilled in the art. All such variations and modifications are intended to be within the scope of the present invention.

What is claimed is:

1. An implant system comprising:
an implantable portion including:
a battery;
a switch for providing power from the battery; and
a Hall sensor, wherein the switch is controlled, at least in part, by output from the Hall sensor; and
an external portion that including:
a first magnet, the magnet for applying a magnetic field to the Hall sensor so as to control the switch;
a power signal transmission module for transmitting an electrical power signal across the skin of a user;
wherein the implantable portion further includes both a second magnet and a receiver module, the receiver module for receiving the power signal across the skin of the user, wherein when the first magnet is placed in a first position, the external portion is held in place on the user based substantially on the magnetic forces between the first magnet and the second magnet, so as to align the power signal transmission module and the receiver module and wherein the switch is configured to latch in position such that the position of the switch does not change upon removal of the magnetic field created by the first magnet.

2. The implant system according to claim 1, wherein when the first magnet is oriented at a first polarity relative to the Hall sensor, the switch is controlled such that power from the battery is interrupted.

3. The implant system according to claim 1, wherein when the first magnet is oriented at a second polarity relative to the Hall sensor, the switch is controlled such that power from the battery is turned on.

4. The implant system according to claim 1, wherein the first magnet applies a magnetic field to the Hall sensor when in a second position relative to the user, so as to control the switch.

5. The implant system according to claim 1, wherein the battery is rechargeable, and the power signal received by the receiver is used to recharge the battery.

6. The implant system according to claim 1, wherein the implantable portion is a cochlear implant, the implantable portion including a stimulator module for producing for the auditory system of the user an electrical stimulation signal representative of an acoustic signal, the stimulator module powered by the battery via the switch.

7. The implant system according to claim 6, wherein the stimulator module includes:
an electrode array;
a microphone for receiving acoustic signals; and
a signal processor for converting acoustic signals received by the microphone into the electrical stimulation signal representative of the acoustic signal, the signal processor stimulating the electrode array with the electrical stimulation signal.

8. The implant system according to claim 1, wherein the battery is rechargeable.

9. A method of operating an implant system, the implant system including an external portion and an implanted portion, the external portion including a first magnet and a power signal transmission module for transmitting an electrical power signal across the skin of a user, the implanted portion including a second magnet, a receiver module for receiving the power signal across the skin of a user, a Hall Sensor, a switch, and a battery, the method comprising:
externally orientating and/or positioning the first magnet in a first arrangement such that the external portion is held in place on the user based substantially on a magnetic force between the first magnet and the second magnet, and such that the power signal transmission module is aligned with the receiver module and the receiver module receives the power signal; alignment
externally orientating and/or positioning the first magnet in a second arrangement, such that the first magnet applies a magnetic field that is sensed by the Hall Sensor, and
controlling the switch in the implanted portion based, at least in part, on output from the Hall Sensor, the switch for providing power from the battery.

10. The method according to claim 9, wherein externally positioning the first magnet in the first arrangement includes orienting the first magnet to be at a first polarity relative to the Hall sensor, whereby the switch is controlled such that power from the battery is interrupted.

11. The method according to claim 10, wherein externally positioning and/or orientating the first magnet in the second arrangement includes orienting the first magnet to be at a second polarity relative to the Hall sensor, whereby the switch is controlled such that power from the battery is turned on.

12. The method according to claim 9, further comprising recharging the battery with the power signal received by the receiver.

13. The method according to claim 9, wherein the implantable portion is a cochlear implant, the method further comprising producing for the auditory system of a user of the cochlear implant an electrical stimulation signal representative of an acoustic signal.

14. The method according to claim 13, wherein producing the electrical stimulation signal includes converting acoustic signals received by an implanted microphone, and stimulating an electrode array with the electrical stimulation signal.

* * * * *